United States Patent
Hammes (10) Patent No.: US 11,099,251 B2
(45) Date of Patent: Aug. 24, 2021

(54) METHOD FOR AUTOMATIC SELECTION OF IMAGING PARAMETERS FOR IMAGING METHODS

(71) Applicant: Siemens Healthcare GmbH, Erlangen (DE)

(72) Inventor: Martin Hammes, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 57 days.

(21) Appl. No.: 16/583,568

(22) Filed: Sep. 26, 2019

(65) Prior Publication Data

US 2020/0096586 A1    Mar. 26, 2020

(30) Foreign Application Priority Data

Sep. 26, 2018   (EP) ..................................... 18196783

(51) Int. Cl.
*G01R 33/54*   (2006.01)
*G06F 17/18*   (2006.01)
*G06T 7/00*   (2017.01)

(52) U.S. Cl.
CPC .......... *G01R 33/543* (2013.01); *G06F 17/18* (2013.01); *G06T 7/0012* (2013.01); *G06T 2207/10088* (2013.01)

(58) Field of Classification Search
CPC ...... G06F 17/18; G06T 7/0012; G01R 33/543
See application file for complete search history.

(56) References Cited

U.S. PATENT DOCUMENTS

| 5,410,249 | A  | * | 4/1995 | Van Yperen | ....... G01R 33/5615 324/307 |
| 6,986,019 | B1 | * | 1/2006 | Bagashev | ........... G06F 12/0804 711/217 |
| 8,989,465 | B2 | * | 3/2015 | Trzasko | ................ G06T 11/003 382/128 |
| 9,345,421 | B2 | * | 5/2016 | Peacock, III | ........ A61B 5/4566 |
| 10,478,134 | B2 | * | 11/2019 | Carmi | .................... G16H 50/30 |
| 10,853,409 | B2 | * | 12/2020 | Wang | ..................... G06N 3/086 |
| 2004/0254439 | A1 | | 12/2004 | Fowkes et al. | |

(Continued)

OTHER PUBLICATIONS

Philips; "Patient-centered CT imaging: New methods for patient-specific optimization"; XP055528950; URL:http://incenter.medical.philips.com/doclib/enc/fetch/2000/4504/577242/577249/586938/587315/iPatient_WP_HR.pdf?nodeid=I3207522&vernum=-2; Stand: Dec. 17, 2015.

(Continued)

*Primary Examiner* — Dixomara Vargas
(74) *Attorney, Agent, or Firm* — Schiff Hardin LLP (57) ABSTRACT

The present disclosure relates to an automatic method for selecting imaging parameters for imaging methods, to a corresponding imaging method, and to a corresponding imaging apparatus comprising a detection algorithm and a selection algorithm. A ranking of at least one qualifying value for potential clinical indications is created. The ranking is based on image data. The ranking is created by means of the detection algorithm. In addition, at least one imaging parameter is selected. The at least one imaging parameter is suitable for producing image data that facilitates a maximum change in the qualifying values in the ranking. The at least one imaging parameter is selected by means of the selection algorithm.

15 Claims, 3 Drawing Sheets

FIG 2

(56) References Cited

U.S. PATENT DOCUMENTS

| | | | |
|---|---|---|---|
| 2005/0209882 A1* | 9/2005 | Jacobsen | G16H 50/20 |
| | | | 705/2 |
| 2009/0118614 A1 | 5/2009 | Sendai | |
| 2014/0369577 A1* | 12/2014 | Collins | G16H 30/20 |
| | | | 382/128 |
| 2015/0080733 A1 | 3/2015 | Yamamoto | |
| 2019/0090826 A1* | 3/2019 | Carmi | A61B 6/037 |
| 2020/0286615 A1* | 9/2020 | Hartung | G16H 50/20 |
| 2021/0003651 A1* | 1/2021 | Kamiguchi | G01R 33/5611 |

OTHER PUBLICATIONS

European Search Report for Patent Application No. 18196783.7, dated Apr. 3, 2019.

* cited by examiner

FIG 3

METHOD FOR AUTOMATIC SELECTION OF IMAGING PARAMETERS FOR IMAGING METHODS

CROSS REFERENCE TO RELATED APPLICATIONS

This patent application claims priority to European Patent Application No. 18196783.7, filed Sep. 26, 2018, which is incorporated herein by reference in its entirety.

BACKGROUND

Field

The present disclosure relates to an automatic method for selecting imaging parameters for imaging methods, including selecting magnetic resonance imaging (MRI) sequences, to a corresponding imaging method, in particular an MRI method, and to a corresponding imaging apparatus, in particular an MRI device, including a detection algorithm and a selection algorithm.

Related Art

When medical image data is created from patients, in particular using an MRI device or magnetic resonance (MR) scanner, but also using a computed tomography (CT) device or similar imaging devices, it is usual to acquire a plurality of image data using different imaging parameters such as sequences or contrasts including different orientations, slice thicknesses, etc. Different imaging parameters are typically used here for different clinical issues. Imaging devices (e.g. MRI devices) can typically be configured such that a combination of different imaging parameters is stored as a protocol. These protocols can then be used to scan patients having specific clinical issues in order to obtain best possible image data for making a diagnosis. For patients with a definite referral or clinical issue, for example "follow-up for multiple sclerosis", a "multiple sclerosis protocol" is usually selected, and is used to produce optimum image data for assessing the clinical issue.

In daily life, however, the problem is more often that patients are referred, or arrive in Radiology, with uncertain findings. The clinical issues are often ill-defined as well (for instance "vague headache"). In these cases, standard protocols are frequently used, and after the acquisition using specific imaging parameters (e.g. sequences/contrasts), a healthcare professional (radiographer) checks the relevant image data or images (sometimes supported by radiologists). If a specific clinical indication is then suspected, the standard protocol is adapted before continuing the imaging process, so that at the end of the imaging process, the radiologist has available the images needed for a best possible assessment of the suspected case. In other words, particular imaging parameters (e.g. contrasts or particular orientations, slice thicknesses, etc.) are adjusted, and the imaging process is continued using a correspondingly adapted protocol.

This approach involves serious disadvantages, however. One disadvantage is that assessing the images is time consuming, in particular when radiologists must be called in first. The time involved here can lead to delays in the process. This is unpleasant for the patient (e.g. time waiting in a tight MR scanner) and may even result in serious harm to the patient if a diagnosis is time-critical (e.g. stroke). Another disadvantage is that the radiographer must be very well trained to be able to select suitable imaging parameters on the basis of the images using the standard protocol. If the radiographer is poorly trained, it may even be the case that the standard protocol is run through, and it is only apparent subsequently during the assessment by the radiologist that additional images or image data using adapted imaging parameters are needed. In this case, the patient must be called back in, involving additional time and costs. Furthermore, a radiologist is not always immediately available for viewing the images directly (in particular for the situation of a poorly trained radiographer). This "live" viewing of the images is also associated with a huge radiologist capacity. If unnecessary image data is acquired and then later it is necessary to use suitably adapted imaging parameters to add even more image data, which is needed for the actual diagnosis, then valuable time is additionally wasted. Moreover, the radiologists must also assess "unnecessary" images, wasting even more capacity.

Nowadays, this problem is solved by deploying qualified personnel (radiographer+radiologist) or by including in the standard protocol the imaging parameters (e.g. contrasts and sequences) for all potential clinical issues. The latter procedure, however, results in the examination lasting a very long time, which can be very unpleasant for the patient, is uneconomic and in the worst case, can even harm the patient (e.g. by wasting time in the event of a stroke).

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure.

The object of the present disclosure is therefore to provide a method, by means of which, best possible imaging parameters for creating image data or images for the assessment are determined in the most time-saving manner possible.

The present disclosure achieves the object by providing a method for automatic selection of imaging parameters as claimed in claim 1, and a corresponding imaging method and an imaging apparatus as claimed in the other independent claims. The subject matter of the respective dependent claims contains advantageous embodiments and developments of the present disclosure. Individual features and feature combinations of the embodiments and developments can be combined with one another in any technically sensible way unless explicitly ruled out below. It is obvious to a person skilled in the art that the further embodiments and developments created thereby are likewise covered by the present disclosure and are hence included in the scope of protection thereof.

In an exemplary embodiment of the present disclosure, a method for automatic selection of imaging parameters includes the following iterative (sequential) steps:

a) Receiving image data, which may originate from an imaging module, for instance by a selection module.
b) Creating a ranking of at least one qualifying value for potential clinical indications. The ranking is based on at least the image data from the previous step. The ranking is created by means of a detection algorithm (DA), for instance by the selection module.
c) Selecting at least one imaging parameter. The at least one imaging parameter is suitable for producing image data that facilitates a maximum change in the qualifying values in the ranking. The at least one imaging parameter is selected by means of a selection algorithm (SA), for instance by the selection module.
d) Sending the selected imaging parameter, for example to the imaging module, for instance by the selection module.

The steps a) to d) are repeated until a predefined termination criterion is met.

In an exemplary embodiment of the present disclosure, an imaging method includes the method for automatic selection of imaging parameters as described above. The imaging method includes the following iterative (sequential) steps:

A) Loading at least one primary imaging parameter, for instance by an imaging module.
B) Performing an imaging process on the basis of the loaded imaging parameter and generating image data, for example using the imaging apparatus, for instance by the imaging module.
C) Sending the generated image data, for example to a selection module, for instance by the imaging module.
a) Receiving the image data, which may originate from the imaging module, for instance by the selection module.
b) Creating a ranking of at least one qualifying value for potential clinical indications. The ranking is based on at least the image data from the previous step. The ranking is created by means of a detection algorithm (DA), for instance by the selection module.
c) Selecting at least one imaging parameter. The at least one imaging parameter is suitable for producing image data that facilitates a maximum change in the qualifying values in the ranking. The at least one imaging parameter is selected by means of a selection algorithm (SA), for instance by the selection module.
d) Sending the selected imaging parameter, for example to the imaging module, for instance by the selection module.
D) Receiving the selected imaging parameter, which may originate from the selection module, for instance by the imaging module.
E) Loading the received imaging parameter, for instance by the imaging module.

The steps B) to C), a) to d), and D) to E) are repeated until a predefined termination criterion is met.

In an exemplary embodiment of the present disclosure, an imaging apparatus includes a controller having an imaging module and a selection module. The controller is configured to perform the imaging method described above. The imaging module is configured to perform the steps A) to C) and D) to E). The selection module is configured to perform the steps a) to d).

In an exemplary embodiment, a combination of the detection algorithm (DA) and the selection algorithm (SA) analyzes acquired image data, and the result of the image analysis has a direct impact on the subsequent behavior of the imaging method or of the imaging apparatus (MR scanner), by imaging parameters (e.g. contrasts or sequences) being selected automatically on the basis of the result of the image analysis.

When a new imaging process is started, in particular for a patient with uncertain findings or an ill-defined clinical issue, initially at least one primary imaging parameter is loaded by the imaging module. This at least one primary imaging parameter may define a standard protocol or a primary protocol or be included thereby. The standard protocol can be used to generate, for example, a localizer image of the part of the body in question or even of the entire patient (spiral CT acquisition). The at least one loaded primary imaging parameter is used to produce (primary) image data, which serves as the basis for the subsequent selection of imaging parameters. The generated (primary) image data is transferred from the imaging module to the selection module for this purpose.

In an exemplary embodiment, once the selection module has received the (primary) image data, the detection algorithm (DA) creates on the basis of the image data a ranking containing probable clinical indications and/or diagnoses. The ranking is based on at least one qualifying value for the clinical indications (e.g. their probability and/or a confidence/significance of this probability). In this process, the detection algorithm (DA) performs an image analysis on the image data. The selection algorithm may be based on artificial intelligence (AI) for this purpose, and may include, for example, a neural network (NN) or a deep NN (DNN) or a convolutional NN (CNN) or alternatively include a support vector machine (SVM) or a random forest classifier (RFC). A detection algorithm based on an NN can be trained initially with training data to detect clinical indications/diagnoses or even just one specific clinical indication/diagnosis in image data. Training-image-datasets for individual imaging parameters (e.g. sequences/contrasts) including technical configuration parameters, which may be stored, for instance, in metadata such as a DICOM header, can be used for this purpose. The NN is trained with the training-image-datasets on the basis of information ("ground truth") about whether a specific clinical indication can be detected in the image data (e.g. in the form of a Boolean variable: 1=clinical indication present; 0=clinical indication not present). Additional information, for instance about which images belong to the same patient, can also be incorporated in the training of the NN. In general, various strategies can be used for the training and testing or final validation of the NN. The trained NN can be used as the detection algorithm (DA). The NN can be applied to the image data (for instance in the DICOM format), and can output at least one associated qualifying value for each clinical indication/diagnosis on which the NN was trained.

Then the selection algorithm (SA) is run on the basis of the ranking containing the qualifying values for the individual clinical indications/diagnoses. The objective of the selection algorithm is to select the at least one imaging parameter for the next imaging process or scan sequence. The at least one imaging parameter is selected or specified here such that in the subsequently acquired image data, there will be a maximum change in the at least one qualifying value for the various clinical indications in the ranking. This maximum change means, for example, that a probability of a clinical indication or diagnosis (e.g. stroke) changes in such a way that the clinical indication/diagnosis can be (reliably) eliminated (e.g. probability of a clinical indication/diagnosis≤5%) or (reliably) confirmed (e.g. $P_{Indication} \geq 95\%$).

Once the termination criterion is met, no more image data is received or analyzed by the detection algorithm, i.e. the ranking created. In addition, no further imaging parameters are selected and sent to the imaging module. The termination criterion ($T_{low}$, $T_{high}$) may be, for example, a low and/or high limit for the probability of a clinical indication/diagnosis (e.g. $0.05 \geq \| 0.95 \leq P_{Indication}$).

The at least one imaging parameter selected by the selection algorithm is transferred from the selection module to the imaging module. After the imaging module has received the at least one imaging parameter, this is loaded by the imaging module for a renewed imaging process. The renewed imaging process is consequently performed using the corresponding at least one imaging parameter, and the image data obtained is supplied again to the selection module.

Once the aforementioned termination criterion is met, again no further imaging process is performed. After the termination criterion is met, the most recently created image data can be output to a user (radiographer and/or doctor or radiologist). It is also optionally possible to output the most recently updated ranking and/or the earlier image data as well. The user can then make a diagnosis for the patient from the most recently created image data and optionally also from the ranking and/or the earlier image data.

In an exemplary embodiment, the selection of the at least one imaging parameter can also to take into account information from the referring doctor (e.g. clinical issue that is meant to be clarified (suspected specific clinical indication/diagnosis)).

The costs for the user fall as a result of avoiding, or reducing the number of, unnecessary re-scans and as a result of the lower personnel effort. Patients benefit from this technical solution because they have shorter scan times thanks to establishing more quickly which (potential) findings exist, and because they receive a better and/or more complete diagnosis. Moreover, even when information from the referring doctor is non-existent or incomplete, it is possible to generate image data quickly that allows the (previously unknown) most likely clinical indication or diagnosis of the patient to be clarified (confirmed or eliminated), because the information from the referring doctor is needed only as an option by the dynamic protocol composed of detection algorithm (DA) and selection algorithm (SA).

In an exemplary embodiment of the present disclosure, selecting the at least one imaging parameter in step c) is performed by the selection algorithm (SA) by means of a data table and/or by means of a model.

In an exemplary embodiment, the selection algorithm is configured to optimize the next imaging process by selecting at least one best possible imaging parameter (e.g. sequence or contrast) for the imaging method or the imaging apparatus (e.g. MR scanner). The basis for the selection is the result from the preceding detection algorithm (DA) (in particular the probability of the existence of a/a plurality of specific clinical indication(s)/diagnosis/diagnoses and/or the confidence(s) of this probability/these probabilities).

The at least one imaging parameter can be selected in a "memory-based" manner on the basis of the data table, in which case the information on the imaging parameters (=selection options, e.g. sequences and other settings) and their attributes is held in the data table. For example, the table can contain three fields per imaging parameter:

1. Imaging parameter (e.g. scan sequence and sequence settings (e.g. FLAIR, "slice thickness", etc.)).
2. Imaging attributes (e.g. duration, "breath hold [yes/no]", etc.)
3. Information content for clinical indications (e.g. Boolean [yes=has information value; no=has no information value] or continuous [0%=no information value to 100%=disease can be detected solely on the basis of this imaging parameter or of this protocol]).

Different selection algorithms can be applied to this data table. For example, first the imaging parameters in the data table can be searched, and the option (imaging parameters and imaging attributes) for which the relevant search criteria apply can be selected. Then, the selected at least one imaging parameter can be transferred to the imaging method or the imaging apparatus for the purpose of configuration, so that now the renewed imaging process can be initiated on the basis of the selected option.

In an exemplary embodiment, the at least one imaging parameter is (additionally or alternatively) selected in a "model-based" manner on the basis of the model. The information on the preferred at least one imaging parameter is stored as weights in a mathematical model (e.g. an NN). An NN can be trained on the basis of the user behavior and/or the usage frequency:

1. Train the NN (including testing and validation) with clinical indications and imaging parameters typical thereof (sequences and sequence settings for the diagnosis, or protocols) as the training dataset.
2. Use the trained NN to select the next at least one imaging parameter (e.g. scan sequence):
   a. Select the imaging parameter (scan sequence) that has been used by the most users for diagnosing a specific clinical indication/diagnosis (e.g. max(frequency clinical indication: tumor))
   b. Select the imaging parameter (e.g. scan sequence) that has been used by the most users on average for diagnosing all clinical indications/diagnoses (e.g. max(average[frequency all clinical indications]))

The data table and the model can also be combined with each other.

There is also the possibility to insert a feedback loop between the detection algorithm (DA) and the selection algorithm (SA), so that after the next imaging process has been selected, and after the detection algorithm (DA) has determined the new ranking, this information is passed back to the selection algorithm (SA) and hence can be used, for instance, to improve the information in the data table or to adapt the model, or more precisely the weights in the NN, of the selection algorithm (SA).

The selection of the imaging parameters by the selection algorithm (SA) by means of a data table can be implemented particularly simply and is therefore economic. If, as an alternative or in addition thereto, the imaging parameters are selected by means of a model (e.g. NN), a reliable selection means is available even when there are a multiplicity of selection options that are very similar to one another.

In an exemplary embodiment of the present disclosure, the termination criterion is met when a qualifying value of at least one of the clinical indications in the ranking meets a predetermined limit criterion (e.g. threshold value for confidence (confidence threshold)) or when all the possible imaging parameters have been cycled through.

In particular, the continued selection of imaging parameters and renewed imaging process can be terminated if there is a high probability of one or more clinical indications/diagnoses being present. Additionally or alternatively, the continued selection of imaging parameters and renewed imaging process can be terminated also if one or more clinical indications/diagnoses can be eliminated with a high probability. In an exemplary embodiment, the method for selection and/or the imaging method can be terminated if the at least one qualifying value (e.g. probability of a clinical indication/diagnosis $P_{Indication}$ and/or the confidence thereof $C_{Indication}$) of at least one clinical indication/diagnosis in the ranking meets the termination criterion $T_{low} \leq 10\%$, preferably $T_{low} \leq 5\%$, more preferably $T_{low} \leq 2\%$, most preferably $T_{low} \leq 1\%$ and/or $T_{high} \geq 90\%$, preferably $T_{high} \geq 95\%$, more preferably $T_{high} \geq 98\%$, most preferably $T_{high} \geq 99\%$. Different termination criteria ($T^{Indication}$, $T^{Confidence}$) can be defined for different qualifying values.

$$(P_{Indication} \leq T_{low}^{Indication} \vee P_{Indication} \geq T_{high}^{Indication}) \vee (C_{Indication} \geq T^{Confidence})$$

Alternatively, in an exemplary embodiment, the method for automatic selection and/or the imaging method can be terminated when all the possible imaging parameters eligible for the clinical indications in the ranking have been cycled through.

A restrictive or less restrictive termination criterion can be preset depending on which clinical indication and/or diagnosis needs to be clarified. This helps to optimize the number of iterations of the automatic selection of imaging parameters. The time required for the method for automatic selection and/or for the imaging method can hence be reduced. The user (e.g. radiologist or radiographer) thus has the facility to control via the termination criteria (e.g. confidence threshold) the behavior of the imaging apparatus and/or of the imaging method.

In an exemplary embodiment of the present disclosure, in step c), the maximum change in the qualifying values in the ranking is based on a maximum change in one of the qualifying values of a single clinical indication in the ranking or on a cumulative maximum change in qualifying values of a plurality of clinical indications in the ranking.

If a specific clinical indication and/or diagnosis is meant to be clarified (confirmed or eliminated with a high degree of certainty), the selection algorithm (SA) can select the at least one imaging parameter such that there is a maximum change in the at least one qualifying value only for the clinical indication/diagnosis to be clarified, so that after a renewed imaging process using the correspondingly selected at least one imaging parameter, there is as great an improvement as possible in the ability to confirm or eliminate, on the basis of the new image data, the clinical indication/diagnosis to be clarified. Alternatively, a maximum possible change can also be made in the least one qualifying value for a plurality of clinical indications/diagnoses, or as many clinical indications/diagnoses as possible, in the ranking. This is done by summing (the absolute values of) the changes in the at least one qualifying value into the cumulative change, and then determining the cumulative maximum change on the basis thereof.

In an exemplary embodiment, the selection algorithm (SA) performs the selection on the basis of the following criteria:

a. Focus on a broad improvement in the at least one qualifying value (e.g. probability or confidence):
   The at least one imaging parameter (e.g. sequence or contrast) is selected that promises a maximum improvement in the at least one qualifying value for as many clinical indications/diagnoses as possible in the ranking (cumulative maximum change).
   "Select the at least one imaging parameter that for all potential clinical indications has the highest information content (i.e. e.g. results in the greatest improvement in the probability and/or the confidence in the probability)
   →Max(Σ(information content for all potential clinical indications))

b. Focus on a specific improvement in the at least one qualifying value (single maximum change):
   The at least one imaging parameter is selected that promises a maximum improvement in the at least one qualifying value for a specific clinical indication/diagnosis (e.g. because a specific diagnosis can be eliminated reliably by means of a specific sequence).
   "Select the at least one imaging parameter that for a specific clinical indication has the highest information content (i.e. e.g. results in the greatest improvement in the probability and/or the confidence in the probability)
   →Max(information content of one clinical indication)

b.1. A variant of criterion b. is, for example, seeking to achieve a maximum improvement in the confidence only for the clinical indication that currently has the highest or lowest probability, and selecting the next imaging parameter (e.g. sequence) on the basis of this criterion.

b.2. Conversely, it is possible to seek to eliminate reliably the clinical indication that is the least probable, and therefore to select the next imaging parameter such that there is a maximum improvement in the confidence for this clinical indication.

b.3. The focus may also be placed on a specific clinical indication if a specific clinical indication is already suspected. In this case, the at least one imaging parameter can be selected such that a high confidence for the selected indication is achieved as quickly as possible. A procedure of this type can be helpful, for example, when examining urgent cases such as patients with a suspected stroke.

c. Combination search: e.g. maximum information content (criterion a.) for minimum possible time.

d. "Subsample search": focus on avoiding specific imaging parameters (sequences). This procedure can be combined with the preceding criteria a. to c. The imaging parameters can be selected such that specific imaging parameters (e.g. having specific imaging attributes (e.g. duration, "breath hold", contrast agent, etc.)) are avoided while still achieving a maximum possible change in the at least one qualifying value (e.g. probability or confidence). A procedure of this type is helpful, for example, when the intention is to manage as far as possible without contrast agent, "breath hold" or loud sequences (e.g. diffusion). Using this criterion, the selection algorithm (SA) can help to select the sequences such that, for example, a sufficient confidence is achieved without the sequences placing a strain on the patient.

"Search only within the imaging parameters that have specific imaging attributes (e.g. without requirement for breath hold)"

By selecting suitable criteria for the selection algorithm (SA), the user (radiologist/radiographer) can direct the imaging method systematically in a specific direction should this be desired or needed.

In an exemplary embodiment of the present disclosure, the at least one qualifying value is a probability of the clinical indications or a confidence of a probability of the clinical indications.

The selection algorithm (SA) selects the at least one imaging parameter (e.g. sequence or contrast) on the basis of the probabilities ($P_{Indication}$) Indication) and/or the confidences ($C_{Indication}$) of the clinical indications in the ranking. It is hence possible for the systematic selection of MRI sequences by the selection algorithm (SA) to take into account, or for the selection to be based on, for example, the probability that a brain tumor exists, and the confidence of this probability, which is based on the analysis of the earlier image data by the detection algorithm (DA).

The probability of clinical indications allows the selection of the imaging parameters for the renewed imaging process to be tightly focused in order to pursue further only the most plausible clinical indications/diagnoses. The confidence of this probability allows the further imaging process to be controlled by the selection of the imaging parameters such that using the resultant image data, the user (e.g. radiologist or radiographer) only makes diagnoses with a high degree of certainty.

In an exemplary embodiment of the present disclosure, in step b), creating the ranking is based on the image data from all the previous iterations.

In creating the ranking of potential clinical indications, the detection algorithm (DA) takes into account not just the image data that has just been transferred to the selection module, but also earlier image data from previous iterations of the imaging method. The detection algorithm (DA) can also take into account image data that was created at an earlier time, for instance during a previous tumor staging.

In particular a detection algorithm including an NN can use additional image data from the same patient to make more accurate statements (e.g. higher confidence of the probabilities of the potential clinical indications), and hence create a more reliable ranking.

In an exemplary embodiment of the present disclosure, the at least one imaging parameter is a magnetic resonance imaging (MRI) sequence.

In an exemplary embodiment, the imaging method is an MRI method.

In an exemplary embodiment, the imaging apparatus is an MRI device.

In particular for MRI devices or the MRI methods, the large number of different MRI sequences, which include a multitude of different contrasts, slice thicknesses, pulse patterns, etc., can create a large amount of different image data, which in each case is particularly suitable for different clinical indications and/or diagnoses. Thus the automatic selection of the MRI sequences can save a particularly large amount of time for MRI devices/methods and achieve a particularly large increase in the certainty with which a diagnosis is made by the user.

In an exemplary embodiment, the primary imaging parameter has been selected on the basis of a primary issue (e.g. information from the referring doctor).

If a primary issue is known, for example "suspected stroke", or in the case of a planned tumor staging, this information is used to select the at least one primary imaging parameter (e.g. sequence or contrast) such that the resultant (primary) image data is already as good as possible for assessing the clinical issue/diagnosis that is based on the primary issue.

The duration and quality of the imaging process can be increased further by taking into account the primary issue.

In an exemplary embodiment, when the predefined termination criterion is met, at least the most recently generated image data or the most recently created ranking is output.

Figure 1:
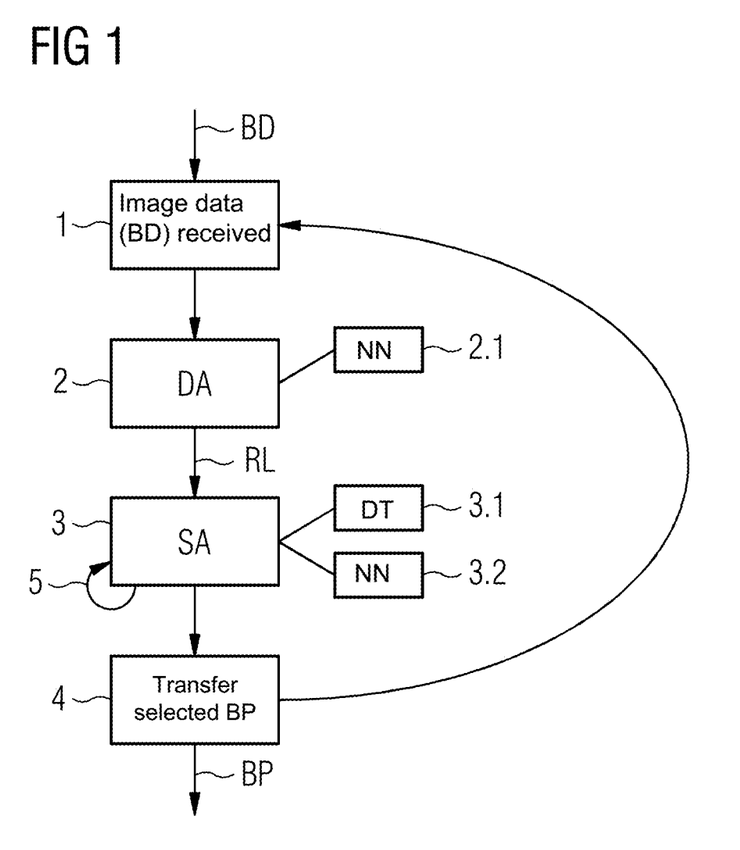
FIG. 1 shows a schematic flow diagram of a method for automatic selection of imaging parameters according to an exemplary embodiment of the present disclosure.

FIG. 1 shows a schematic flow diagram of a method for automatic selection of imaging parameters according to the present disclosure. Image data BD is received 1 in the first step a). The image data may have been created by an image processing apparatus such as, for example, a magnetic resonance imaging (MRI) device, a computed tomography (CT) device, ultrasound device, or the like. The image data BD can originate from an imaging module of the image processing apparatus, and be received, for example, by a selection module of the imaging processing apparatus. A ranking RL of at least one qualifying value for potential clinical indications is created 2 in a second step b) on the basis of this received image data BD. The creation 2 can additionally also be based on image data BD from previous iterations or also on image data from other imaging processes. The ranking RL is created 2 by means of a detection algorithm (DA). The detection algorithm can be executed by the selection module, for example. After the ranking RL has been created, at least one imaging parameter BP is selected 3 in a third step c). The at least one imaging parameter BP is suitable for producing in a subsequent (renewed) imaging process (e.g. MRI scan) image data BD that facilitates a maximum change in the qualifying values in the ranking RL. The at least one imaging parameter BP is selected 3 by means of a selection algorithm (SA). The selection algorithm can be executed by the selection module, for example. The selected at least one imaging parameter BP is then transferred, for instance from the selection module to the imaging module, by sending 4 the selected imaging parameter BP in a fourth step d). The first to fourth steps are repeated iteratively until a termination criterion is met.

In an exemplary embodiment, imaging parameters are selected automatically by a dynamic diagnosis elimination protocol, which essentially includes the detection algorithm DA and the selection algorithm SA.

The detection algorithm DA indicates a probability $P_{Indication}$ for the existence of a specific clinical indication/disease. At the same time, information about the level of "reliability" of this ascertained probability $P_{Indication}$ is provided by determining a confidence $C_{Indication}$ of the probability. The image data BD that has just been received or all of the data received hitherto forms the basis for this evaluation. In other words, an image analysis is performed in which, for example, there is just 1 contrast in the 1st iteration, there are 2 contrasts in the 2nd iteration, 3 contrasts in the 3rd iteration, and so on, which the detection algorithm DA analyzes in order to create the ranking. The image analysis can be performed by the detection algorithm using various techniques. In an exemplary embodiment, Neural Networks (NN) 2.1, in particular deep NN (DNN) and subcategories (e.g. convolutional NN (CNN)) can be used for this purpose. Support vector machines (SVMs) and random forest classifiers (RFCs) are also possible. In an exemplary embodiment, the procedure for training and subsequent use in an MRI device (MR scanner) is described here for an NN 2.1:

1. Train & test the NN (supervised learning):
   Training data:
   image datasets for individual sequences/contrasts including technical configuration parameters (typically stored in the DICOM header)
   "ground truth": information about whether a specific clinical indication can be detected in the image, in the form a Boolean variable (1=clinical indication present; 0=clinical indication not present). For instance in image data from healthy patients, the Boolean variables=0 for all clinical indications.
   Optionally additional training information such as, for instance, which image data belongs to the same patient.
   Various strategies can be used for the training, testing and final validation.
2. Use the NN 2.1 to generate the qualifying values, for example probabilities of various clinical indications $P_{Indication}$ and confidences of these probabilities $C_{Indication}$.
   a. Load the image data from previously performed imaging processes, for instance MRI scans, in the DICOM format.
   b. Apply the trained NN 2.1, which determines the probabilities $P_{Indication}$ and confidences $C_{Indication}$ for the potential clinical indications (e.g. brain tumor).
   c. Output:
   The probability of the existence of a specific clinical indication/diagnosis $P_{Indication}$.
   The confidence (significance) for these probabilities $C_{Indication}$.

In an exemplary embodiment, the selection algorithm SA, which builds upon the detection algorithm DA, selects the next at least one imaging parameter, in this case the next scan sequence (including corresponding sequence settings) for the MRI device. The basis for the decision or selection is the result, namely the ranking RL, from the preceding detection algorithm DA (in particular the probability $P_{Indication}$ of the existence of a specific clinical indication and/or the confidence for these probabilities $C_{Indication}$). There are various ways of performing the selection of the next scan sequence.

One way is "memory-based", in which the information on the imaging parameters (scan sequences and scan settings) and attributes of the imaging parameters are held in a data table 3.1. The data table 3.1 contains three fields per imaging parameter:
1. Scan sequence+sequence settings (e.g. FLAIR, "slice thickness" 2 mm, etc.)
2. Imaging attributes (e.g. duration, "breath hold [yes/no]", etc.)
3. Information content for clinical indications (e.g. Boolean (yes=has information value; no=has no information value) or continuous (0%=no information value to 100%=disease can be detected solely on the basis of this imaging scan sequence)).

Different selection algorithms can be applied to this data table 3.1. Example procedure:
1. Search the imaging parameters in the data table and select the imaging parameters (scan sequence and sequence settings) for which the relevant search criteria apply; for example:

a. Focus on a broad improvement in the at least one qualifying value (e.g. probability or confidence):
The at least one imaging parameter (e.g. sequence or contrast) is selected that promises a maximum improvement in the at least one qualifying value for as many clinical indications/diagnoses as possible in the ranking (cumulative maximum change).
"Select the at least one imaging parameter that for all potential clinical indications has the highest information content (i.e. e.g. results in the greatest improvement in the probability and/or the confidence in the probability)
→Max(Σ(information content for all potential clinical indications))
b. Focus on a specific improvement in the at least one qualifying value (single maximum change):
The at least one imaging parameter is selected that promises a maximum improvement in the at least one qualifying value for a specific clinical indication/diagnosis (e.g. because a specific diagnosis can be eliminated reliably by means of a specific sequence).
"Select the at least one imaging parameter that for a specific clinical indication has the highest information content (i.e. e.g. results in the greatest improvement in the probability and/or the confidence in the probability)
→Max(information content of one clinical indication)
b.1. A variant of criterion b. is, for example, seeking to achieve a maximum improvement in the confidence only for the clinical indication that currently has the highest or lowest probability, and selecting the next imaging parameter (e.g. sequence) on the basis of this criterion.
b.2. Conversely, it is possible to seek to eliminate reliably the clinical indication that is the least probable, and therefore to select the next imaging parameter such that there is a maximum improvement in the confidence for this clinical indication.
b.3. The focus may also be placed on a specific clinical indication if a specific clinical indication is already suspected. In this case, the at least one imaging parameter can be selected such that a high confidence for the selected indication is achieved as quickly as possible. A procedure of this type can be helpful, for example, when examining urgent cases such as patients with a suspected stroke.
c. Combination search: e.g. maximum information content (criterion a.) for minimum possible time.
d. "Subsample search": focus on avoiding specific imaging parameters (sequences). This procedure can be combined with the preceding criteria a. to c. The imaging parameters can be selected such that specific imaging parameters (e.g. having specific imaging attributes (e.g. duration, "breath hold", contrast agent, etc.)) are avoided while still achieving a maximum possible change in the at least one qualifying value (e.g. probability or confidence). A procedure of this type is helpful, for example, when the intention is to manage as far as possible without contrast agent, "breath hold" or loud sequences (e.g. diffusion). Using this criterion, the selection algorithm (SA) can help to select the sequences such that, for example, a sufficient confidence is achieved without the sequences placing a strain on the patient.
"Search only within the imaging parameters that have specific imaging attributes (e.g. without requirement for breath hold)"
2. Transfer the selected imaging parameters to the MR scanner for the purpose of configuration, so that now the user can initiate the MRI scan on the basis of the selected MRI sequence.

In an exemplary embodiment, the imaging parameters (scan sequences) is selected additionally or alternatively in a "model-based" manner. The information on the preferred imaging parameter (scan sequence) is stored as weights in a mathematical model (e.g. NN) 3.2. The NN can be trained, for example, on the basis of the user behavior/usage frequency:
1. Train the network (including testing & validation):
   Input-data for the training:
      Clinical indications and typical imaging parameters (sequences and sequence settings) for the diagnosis (protocols).
2. Use the trained NN to select the next imaging parameter (scan sequence). It is possible to use similar decision criteria to those described above for the "memory-based" selection algorithm SA using a data table:
a. Select the scan sequence that has been used by the most users for diagnosing a specific clinical issue:
   max(frequency of a clinical indication)
b. Select the scan sequence that has been used by the most users on average for diagnosing all clinical issues:
   max(average(frequency of all clinical indications))
c. and d. are analogous to the decision criteria described above.

There is the option to insert a feedback loop 5 between the detection algorithm DA and the selection algorithm SA. In this case, after the next scan sequence has been selected and the detection algorithm DA has calculated the new ranking RL, this information is passed back to the selection algorithm SA. The fed-back information is thus used, for example, to improve the information in the data table 3.1 or to adapt the weights in the model (NN) 3.2.

The iteration through the first to fourth steps is terminated once the termination criterion is met. The termination criterion specifies, for example, a minimum probability ($T_{high}^{Indication}$) for which a clinical indication must exist in order to be able to confirm this clinical indication. Conversely, it is also possible to define a maximum probability as the termination criterion ($T_{low}^{Indication}$), up to which a clinical indication can be confirmed as not existing. Additionally or alternatively, a minimum confidence can be specified as the termination criterion ($T^{Confidence}$) above which a statement about the probability of a clinical indication can be deemed reliable.

A possible output of a ranking RL from the detection algorithm DA based on image data BD from a head of a patient is presented below in a first table by way of example.

| Clinical indication | Probability | Confidence |
|---|---|---|
| Tumor | 5% | 3% |
| Multiple sclerosis | 2% | 5% |
| Alzheimer's | 1% | 2% |
| Stroke | 1% | 6% |

The second table below presents by way of example the qualifying values in a ranking RL after a further iteration. In this case, the selection algorithm SA has selected by way of example an MRI sequence that can be used to eliminate (low probability) reliably (high confidence) the clinical indication "stroke". This can be achieved by the criterion b.1 described above.

| Clinical indication | Probability | Confidence |
|---|---|---|
| Tumor | 5% | 3% |
| Multiple sclerosis | 1% | 40% |
| Alzheimer's | 1% | 60% |
| Stroke | 0.1% | 98% |

In the third table, which is given below, the ranking RL from the second table has been updated by a subsequent iteration based on image data that originates from an imaging process using imaging parameters (MRI sequence) that also make it possible to ascertain with the greatest possible certainty as far as possible all the other clinical indications. This is possible by means of the criterion a. described above.

| Clinical indication | Probability | Confidence |
|---|---|---|
| Tumor | 10% | 75% |
| Multiple sclerosis | 1% | 80% |
| Alzheimer's | 1% | 60% |
| Stroke | 0.1% | 99% |

Figure 2:
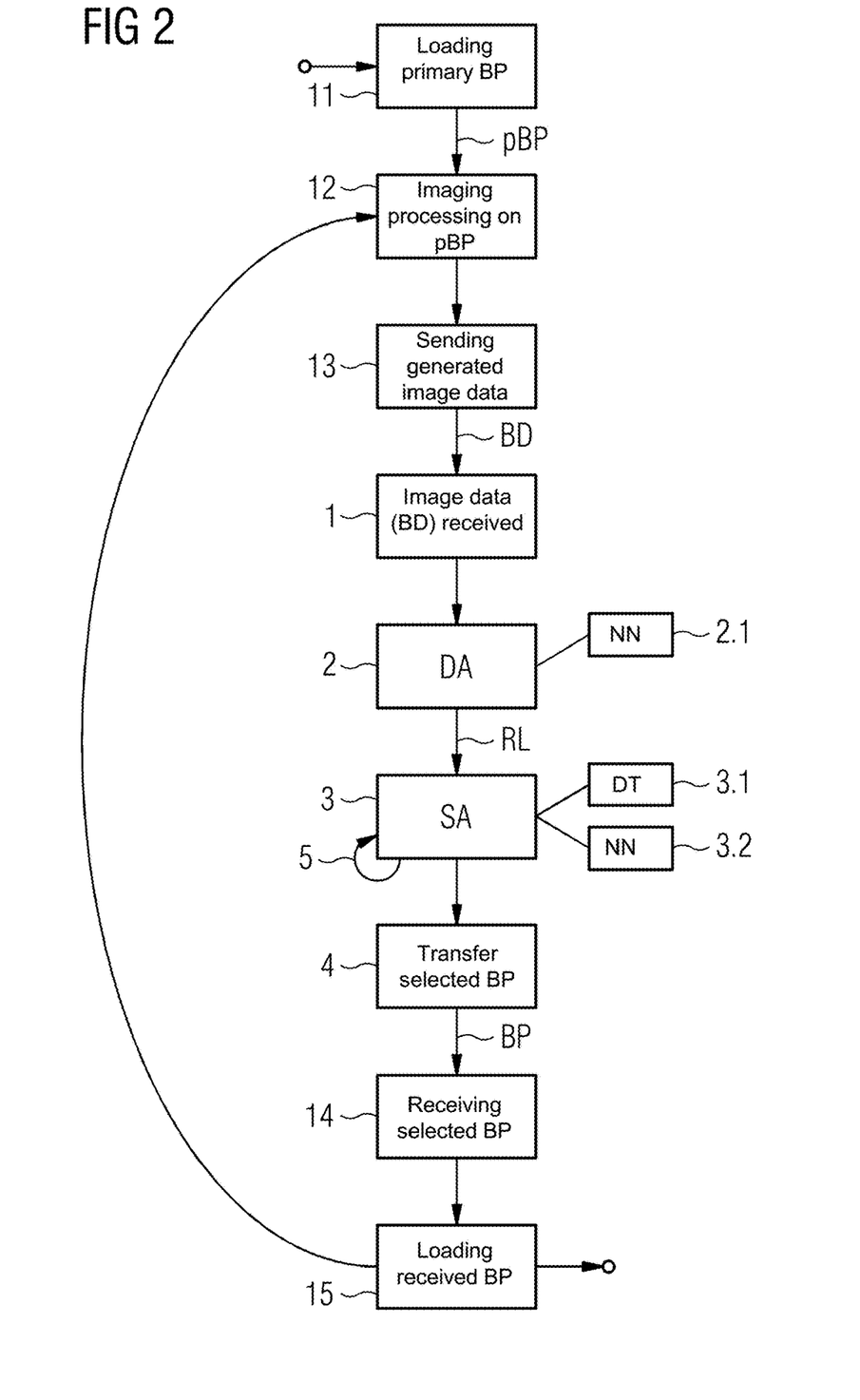
FIG. 2 shows a schematic flow diagram of an imaging method, according to an exemplary embodiment, that includes the method for automatic selection of imaging parameters from FIG. 1.

FIG. 2 shows a schematic flow diagram of an imaging method that includes the method for automatic selection of imaging parameters from FIG. 1. Only the additional steps of the imaging method are described below. In a first imaging step A), at least one primary imaging parameter pBP is loaded 11, for instance by an imaging module. Then in a second imaging step, an imaging process is performed 12 on the basis of the loaded imaging parameter pBP/BP, and image data BD is generated (for example using an imaging apparatus such as an MR scanner by means of its imaging module). Then in a third imaging step, the generated image data BD is sent 13 (e.g. to a selection module of the MR scanner by its imaging module). This is followed by the four steps of the method for automatic selection of imaging parameters BP, as described above. After at least one imaging parameter BP has been selected automatically, the selected imaging parameter BP, which may originate from the selection module of the MR scanner, is received 14 by the imaging module thereof in a fourth imaging step. Finally, in a fifth imaging step, the received imaging parameter BP is loaded 15, for example by the imaging module of the MR scanner.

The second to third imaging steps, the first to fourth steps of the method for automatic selection of imaging parameters, and the fourth to fifth imaging steps are performed iteratively until the termination criterion is met, as described earlier.

Figure 3:
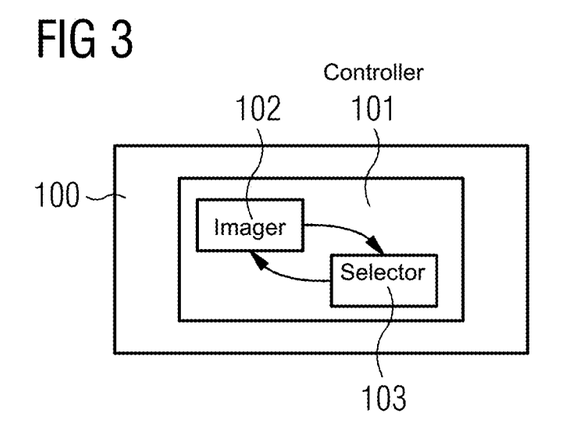
FIG. 3 shows a schematic imaging apparatus according to an exemplary embodiment of the present disclosure that includes a controller configured to perform the imaging method from FIG. 2.

FIG. 3 shows a schematic imaging apparatus 100 according to an exemplary embodiment. In an exemplary embodiment, the imaging apparatus 100 includes a controller 101 configured to perform one or more imaging processing operations. In an exemplary embodiment, the controller 101 is configured to perform one or more imaging methods of the present disclosure, including the imaging method described with reference to FIG. 2. In an exemplary embodiment, the imaging apparatus 100 (e.g. an MRI device (MR scanner)), includes controller 101 including an imaging module (imager) 102 and a selection module (selector) 103. The imaging module 102 and selection module 103 can be referred to as an imaging controller 102 and a selection controller 103, respectively. In an exemplary embodiment, the imaging module 102 is configured to execute the first to fifth imaging steps (11, 12, 13, 14, and 15 as shown in FIG. 2). The selection module 103 is configured to execute the first to fourth steps (1, 2, 3, 4) of the method for automatic selection of imaging parameters. In an exemplary embodiment, the imaging module 102 sends generated image data BD to the selection module 103, and the selection module 103 sends selected imaging parameters BP and optionally determined rankings RL to the imaging module 102. In an exemplary embodiment, the controller 101 includes or is comprised of one or more data processing units such as, for example, microcontrollers (μC), integrated circuits, application-specific integrated circuits (ASIC), application-specific standard products (ASSP), digital signal processors (DSP), field programmable (logic) gate arrays (FPGA), and the like. In an exemplary embodiment, the imaging module 102 and/or the selection module 103 are implemented in the data processing unit(s) of the controller 101 or can each include dedicated data processing units, which are in communication with the controller 101. In an exemplary embodiment, the controller 101 (including the imaging module 102 and/or the selection module 103) includes processor circuitry that is configured to perform one or more operations and/or functions of the controller 101 (including one or more operations and/or functions of the imaging and/or selection modules).

Although specific embodiments have been illustrated and described here, it is obvious to a person skilled in the art that there are a multiplicity of alternatives and/or equivalent implementations. It must be recognized that the exemplary designs or embodiments are just examples and are not intended to have any limiting effect whatsoever on the scope, applicability or configuration. In fact, the above summary and detailed description provides a person skilled in the art with sufficient prompting to implement at least one preferred embodiment, where it goes without saying that various alterations in the function and arrangement of those elements described in an exemplary embodiment do not depart from the scope of use presented in the accompanying claims and the legal equivalents thereof. This application is generally intended to cover all adaptations or variations of the specific embodiments discussed here.

In the above detailed description, various features have been combined in one or more examples in order to keep the disclosure brief. It is self-evident that the above description is intended to be illustrative and not restrictive. It is intended to cover all the alternatives, modifications and equivalents that may be included in the disclosure. Numerous other examples will become obvious to a person skilled in the art on studying the above disclosure.

In order to facilitate a thorough understanding of the disclosure, a specific nomenclature is used, which has been used in the above disclosure. In the light of the specification contained therein, however, it will be obvious to a person skilled in the art that the specific details are not needed in order to apply the disclosure. Thus the above descriptions of specific embodiments of the present disclosure are presented for the purpose of illustration and explanation. They are not intended to be exhaustive or to restrict the disclosure to the precise embodiments disclosed above; obviously numerous modifications and variations regarding the aforementioned teaching are possible. The embodiments have been selected and described in order to best explain the principles of the disclosure and its practical applications, and hence to give other professionals the opportunity to apply in the best way the disclosure and different embodiments using various modifications as seems fit for the particular use. The terms "including" and "in which" are used throughout the specification as equivalents for the respective terms "comprising" and "wherein". In addition, the terms "first", "second", "third", etc. are used merely as a designation and are not intended to place numerical requirements on the objects or to define a specific order of precedence. In the context of the present description and the claims, the conjunction "or" shall be understood to be inclusive ("and/or") and not exclusive ("either . . . or").

The aforementioned description of the specific embodiments will so fully reveal the general nature of the disclosure that others can, by applying knowledge within the skill of the art, readily modify and/or adapt for various applications such specific embodiments, without undue experimentation, and without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computers, processors, controllers, or other devices executing the firmware, software, routines, instructions, etc. Further, any of the implementation variations may be carried out by a general purpose computer.

For the purposes of this discussion, the term "processor circuitry" shall be understood to be circuit(s), processor(s), logic, or a combination thereof. A circuit includes an analog circuit, a digital circuit, state machine logic, programmable processing circuit, other structural electronic hardware, or a combination thereof. A processor includes a microprocessor, a digital signal processor (DSP), central processing unit (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A method for automatic selection of imaging parameters, comprising:
   receiving image data from an imaging scanner;
   creating, using a detection algorithm, a ranking of a set of values based on the received image data, the set of values including a plurality of probability values and a plurality of confidence values, with each respective one of the plurality of probability values indicating a probability that a respective abnormal clinical issue is detected in the image data, and each respective one of the plurality of confidence values corresponding to a respective one of the plurality of probability values and indicating a respective confidence level associated with the probability that the respective abnormal clinical issue is detected,
   wherein ranking the set of values includes ranking the plurality of probability values from a highest probability value to a lowest probability value;
   selecting, using a selection algorithm, at least one imaging parameter from among imaging parameters used by the imaging scanner to produce subsequent image data that facilitates a maximum change in at least one of (i) the plurality of probability values, and/or (ii) the plurality of confidence values in the ranking of the set of values when the detection algorithm is applied to the next subsequently-received image data; and
   wherein subsequent image data is received for a number of subsequent scans performed by the imaging scanner, and the creation of the set of values and selection of the at least one imaging parameter are repeated for each of the number of scans until a predefined termination criterion is met.

2. The method as claimed in claim 1, wherein selecting the at least one imaging parameter performed by the selection algorithm uses a data table or a model.

3. The method as claimed in claim 1, wherein the termination criterion is met when at least one of (i) the plurality of probability values, and/or (ii) the plurality of confidence values satisfies a predetermined limit criterion.

4. The method as claimed in claim 1, wherein, in the selecting the at least one imaging parameter, the maximum change in at least one of (i) the plurality of probability values, and/or (ii) the plurality of confidence values is based on a maximum change in at least one of (i) the plurality of probability values, and/or (ii) the plurality of confidence values of a single abnormal clinical issue associated with the set of values.

5. The method as claimed in claim 1, wherein the ranking of the set of values is created based on the image data from all previous iterations of the method.

6. The method as claimed in claim 1, wherein the at least one imaging parameter is a magnetic resonance imaging (MRI) sequence.

7. The method as claimed in claim 1, wherein the termination criterion is met when each one of a predetermined set of imaging parameters have been selected.

8. The method as claimed in claim 1, wherein the act of selecting the at least one imaging parameter, the maximum change is based on cumulative maximum change in (i) the plurality of probability values, and/or (ii) the plurality of confidence values associated with a plurality of abnormal clinical issues associated with the set of values.

9. The method as claimed in claim 1, wherein the act of selecting the at least one imaging parameter comprises selecting the at least one imaging parameter such that each one of the number of subsequent scans is performed by the imaging scanner to generate respective image data that facilitates the maximum change in at least one of (i) the plurality of probability values, and/or (ii) the plurality of confidence values in the ranking of the set of values for a different abnormal clinical issue.

10. An imaging method comprising:
    by an imager of a magnetic resonance imaging (MRI) scanner, loading at least one primary imaging parameter;
    performing, by the imager, an imaging process based on the loaded at least one primary imaging parameter to generate image data;
    creating, by a selector of the MRI scanner using a detection algorithm, a ranking of a set of values based on the image data, the set of values including a plurality of probability values and a plurality of confidence values, with each respective one of the plurality of probability values indicating a probability that a respective abnormal clinical issue is detected in the image data, and each respective one of the plurality of confidence values corresponding to a respective one of the plurality of probability values and indicating a respective confidence level associated with the probability that the respective abnormal clinical issue is detected,
    wherein ranking the set of values includes ranking the plurality of probability values from a highest probability value to a lowest probability value;
    selecting, using a selection algorithm, at least one imaging parameter from among imaging parameters used by the MRI scanner to produce subsequent image data that facilitates a maximum change in at least one of (i) the plurality of probability values, and/or (ii) the plurality of confidence values in the ranking of the set of values when the detection algorithm is applied to the next subsequently-received image data; and
    loading the selected imaging parameter in the imager of the MRI scanner, and
    wherein the performance of the imaging process, the creation of the ranking of the set of values, the selection of the at least imaging parameter, and the loading of the selecting imaging parameters are repeated for each of a number of subsequent scans performed by the imager until a predefined termination criterion is met.

11. The imaging method as claimed in claim 10, wherein the primary imaging parameter is selected based on a predetermined abnormal clinical issue.

12. The imaging method as claimed in 10, further comprising:
when the predefined termination criterion is met, providing, as an output, a data file corresponding to a most-recently generated image data of the image data generated by the imager.

13. The imaging method as claimed in 10, further comprising:
when the predefined termination criterion is met, providing, as an output, a data file corresponding to a most-recently created ranking of the set of values created via execution of the selection algorithm.

14. An imaging apparatus, comprising:
an image controller configured to:
load at least one primary imaging parameter; and
perform an imaging process based on the loaded at least one primary imaging parameter to generate image data; and
a selection controller configured to:
create, using a detection algorithm, a ranking of a set of value based on the image data, the set of values including a plurality of probability values and a plurality of confidence values, with each respective one of the plurality of probability values indicating a probability that a respective abnormal clinical issue is detected in the image data, and each respective one of the plurality of confidence values corresponding to a respective one of the plurality of probability values and indicating a respective confidence level associated with the probability that the respective abnormal clinical issue is detected,
wherein ranking the set of values includes ranking the plurality of probability values from a highest probability value to a lowest probability value; and
select, using a selection algorithm, at least one imaging parameter suitable from among imaging parameters used by the imaging process to produce subsequent image data that facilitates a maximum change in at least one of (i) the plurality of probability values, and/or (ii) the plurality of confidence values the in the ranking of the set of values when the detection algorithm is applied to the next subsequently-received image data, the selected imaging parameter being loaded into the image controller, and
wherein the performance of the imaging process, the creation of the ranking of the set of values, the selection of the at least imaging parameter, and the loading of the selecting imaging parameters are repeated for each of a number of subsequent scans performed by the imager until a predefined termination criterion is met.

15. The imaging apparatus as claimed in claim 14, wherein the imaging apparatus is a magnetic resonance imaging (MRI) scanner.

* * * * *